(12) United States Patent
Li

(10) Patent No.: US 10,149,611 B2
(45) Date of Patent: Dec. 11, 2018

(54) SERVER AND METHOD FOR SIMULATING CORRECTION OF HUMAN VISUAL ACUITY

(71) Applicant: HON HAI PRECISION INDUSTRY CO., LTD., New Taipei (TW)

(72) Inventor: Wen-Kai Li, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 15/458,700

(22) Filed: Mar. 14, 2017

(65) Prior Publication Data

US 2018/0132712 A1   May 17, 2018

(30) Foreign Application Priority Data

Nov. 11, 2016   (TW) .............................. 105136869 A

(51) Int. Cl.
*A61B 3/00*   (2006.01)
*A61B 3/10*   (2006.01)
*A61B 3/14*   (2006.01)
*A61B 3/117*   (2006.01)
*A61B 3/16*   (2006.01)

(52) U.S. Cl.
CPC .......... *A61B 3/0025* (2013.01); *A61B 3/1005* (2013.01); *A61B 3/1015* (2013.01); *A61B 3/117* (2013.01); *A61B 3/1173* (2013.01); *A61B 3/14* (2013.01); *A61B 3/16* (2013.01); *A61B 3/165* (2013.01)

(58) Field of Classification Search
CPC ........... A61B 3/14; A61B 3/0025; A61B 3/12; A61B 3/102; A61B 3/0058
USPC .................................................. 351/200–246
See application file for complete search history.

(56) References Cited

U.S. PATENT DOCUMENTS

2008/0143960 A1*   6/2008   MacRae ................... A61B 3/04
                                                                   351/230
2015/0221125 A1*   8/2015   Shimizu ............... G06K 9/0061
                                                                   382/128

* cited by examiner

Primary Examiner — Mohammed Hasan
(74) Attorney, Agent, or Firm — ScienBiziP, P.C.

(57) ABSTRACT

A process for simulating correction of human eyeball for better visual acuity includes a processor and coupled memory. The memory stores program for processor to obtain geometric data and a wave-front aberration of human eyeballs and simulate an eyeball model. The eyeball model and an ophthalmic lens model are combined to form a correction system for visual acuity. According to the convex/concave lens imaging rule, and using an object placed in front of the eyeball, a determination is made of an optically uncorrected first image formed at a retina of the eyeball, and a visually-corrected second image formed at the retina of the eyeball. The first object image and the second object image can be output for comparison.

12 Claims, 2 Drawing Sheets

SERVER AND METHOD FOR SIMULATING CORRECTION OF HUMAN VISUAL ACUITY

FIELD

The subject matter relates to simulation of correction of human optical acuity.

BACKGROUND

Ametropia, such as myopia, hyperopia, or astigmatism, is an abnormal refractive condition of eyes in which images fail to focus upon the retina. A user can choose eyeglasses or Laser in Situ Keratomileusis (LASIK) surgery to correct ametropia. However, the effect of ametropia correction cannot be predicted in advance whether the user chooses eyeglasses or LASIK surgery. The user may be not satisfied with the effect of the ametropia correction. Thus, when the user chooses eyeglasses, the eyeglasses need to be modified, which increases the manufacturing cost. When the user chooses the LASIK surgery, which uses an excimer laser to cut or reshape the cornea, the cornea after surgery is often not amenable to further surgery.

BRIEF DESCRIPTION OF THE DRAWINGS

Implementations of the present technology will now be described, by way of example only, with reference to the attached figures.

DETAILED DESCRIPTION

Figure 1:
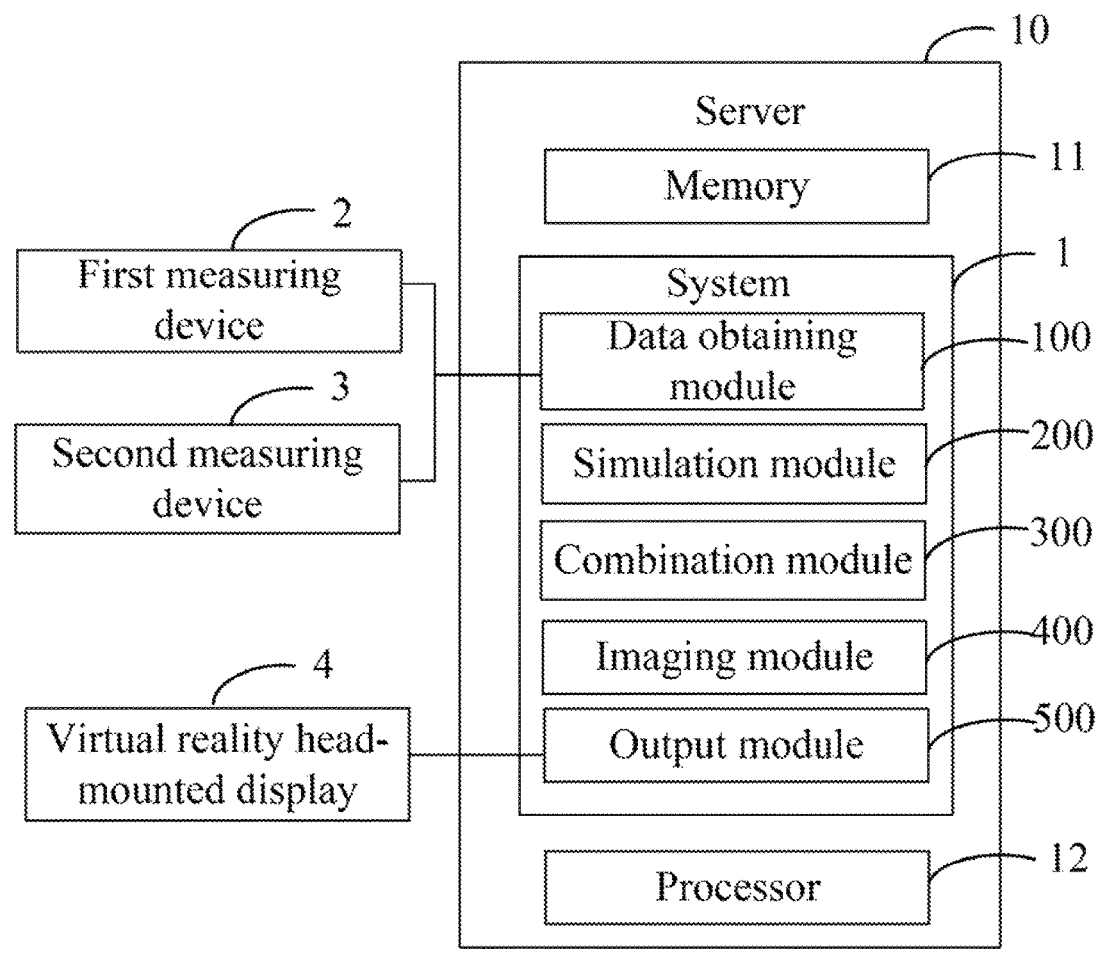
FIG. 1 is a block diagram of an exemplary embodiment of a server for simulating correction of human visual acuity according to the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

In general, the word "module," as used hereinafter, refers to logic embodied in hardware or firmware, or to a collection of software instructions, written in a programming language, such as, for example, Java, C, or assembly. One or more software instructions in the modules may be embedded in firmware. It will be appreciated that modules may comprise connected logic modules, such as gates and flip-flops, and may comprise programmable modules, such as programmable gate arrays or processors. The modules described herein may be implemented as either software and/or hardware modules and may be stored in any type of non-transitory computer-readable storage medium or other computer storage device. The term "comprising," when utilized, means "including, but not necessarily limited to"; it specifically indicates open-ended inclusion or membership in the so-described combination, group, series and the like.

FIG. 1 illustrates an exemplary embodiment of a server 10. The server 10 comprises a memory 11 and at least one processor 12. The memory 11 stores a system 1 for simulating correction of human visual acuity. The system 1 comprises a data obtaining module 100, a simulation module 200, a combination module 300, an imaging module 400, and an output module 500. The modules 100-500 may comprise computerized instructions in the form of one or more programs that are stored in the memory 10 and executed by the at least one processor 12.

The data obtaining module 100 obtains geometric data and a wave-front aberration of at least one human eyeball. In at least one exemplary embodiment, the geometric data comprises central corneal thickness (CCT), anterior chamber depth (ACD), lens thickness (LT), and vitreous chamber depth (VCD), and any combination thereof. The geometric data can further comprise reflective indexes of central corneal, anterior chamber, crystalline lens, and vitreous chamber.

In at least one exemplary embodiment, the server 1 is connected to a first measuring device 2 and a second measuring device 3. The first measuring device 2 measures the geometric data. The second measuring device 3 measures the wave-front aberration. The data obtaining module 100 obtains the geometric data and the wave-front aberration from the first measuring device 2 and the second measuring device 3, respectively. The first measuring device 2 can be a handheld tonometer or a non-contact tonometer. The second measuring device 3 can be a wave-front aberrometer. In other embodiments, the server 1 is connected to an input device (such as keyboard or a mouse, not shown). The data obtaining module 100 obtains the geometric data and the wave-front aberration input through the input device.

The simulation module 200 simulates an eyeball model according to the geometric data and an ophthalmic lens model according to the wave-front aberration. The ophthalmic lens model can be an eyeglass model, a contact lens model, or an intraocular lens model.

The combination module 300 combines the eyeball model and the ophthalmic lens model to form a correction system for human visual acuity. In at least one exemplary embodiment, when the ophthalmic lens model is the eyeglass model, the combination module 300 places the eyeglass model in front of the eyeball model to form the correction system. When the ophthalmic lens model is the contact lens model, the combination module 300 places the contact lens model in contact with the eyeball model to form the correction system. When the ophthalmic lens model is the intraocular lens model, the combination module 300 removes the crystalline lens of the eyeball model and embeds the intraocular lens model into the eyeball model to form the correction system.

The imaging module 400 determines, according to a convex/concave lens imaging rule, a first image formed at a retina of the eyeball module when an object is placed in front of the eyeball module, and a second image formed at the retina of the eyeball module when the object is placed in front of the correction system.

For example, when the object is placed in front of the eyeball module, which functions as a convex lens, the first image may be formed behind the eyeball module (at the retina of the eyeball module) according to the convex lens imaging rule. The first image can simulate instant and uncorrected human visual acuity. When the object is then placed in front of the correction system, which functions as a convex lens, the second image may be formed behind the correction system (at the retina of the eyeball module) according to the convex lens imaging rule. The second image can simulate a corrected human visual acuity.

The output module 500 outputs the first object image and the second object image. A comparison between the first object image and the second object image can help the user to understand the correction of human visual acuity. In at least one exemplary embodiment, the server 1 is connected to a virtual reality head-mounted display 4. The output module 500 can output the first object image and the second object image to the virtual reality head-mounted display 4, thereby improving the user experience.

Figure 2:
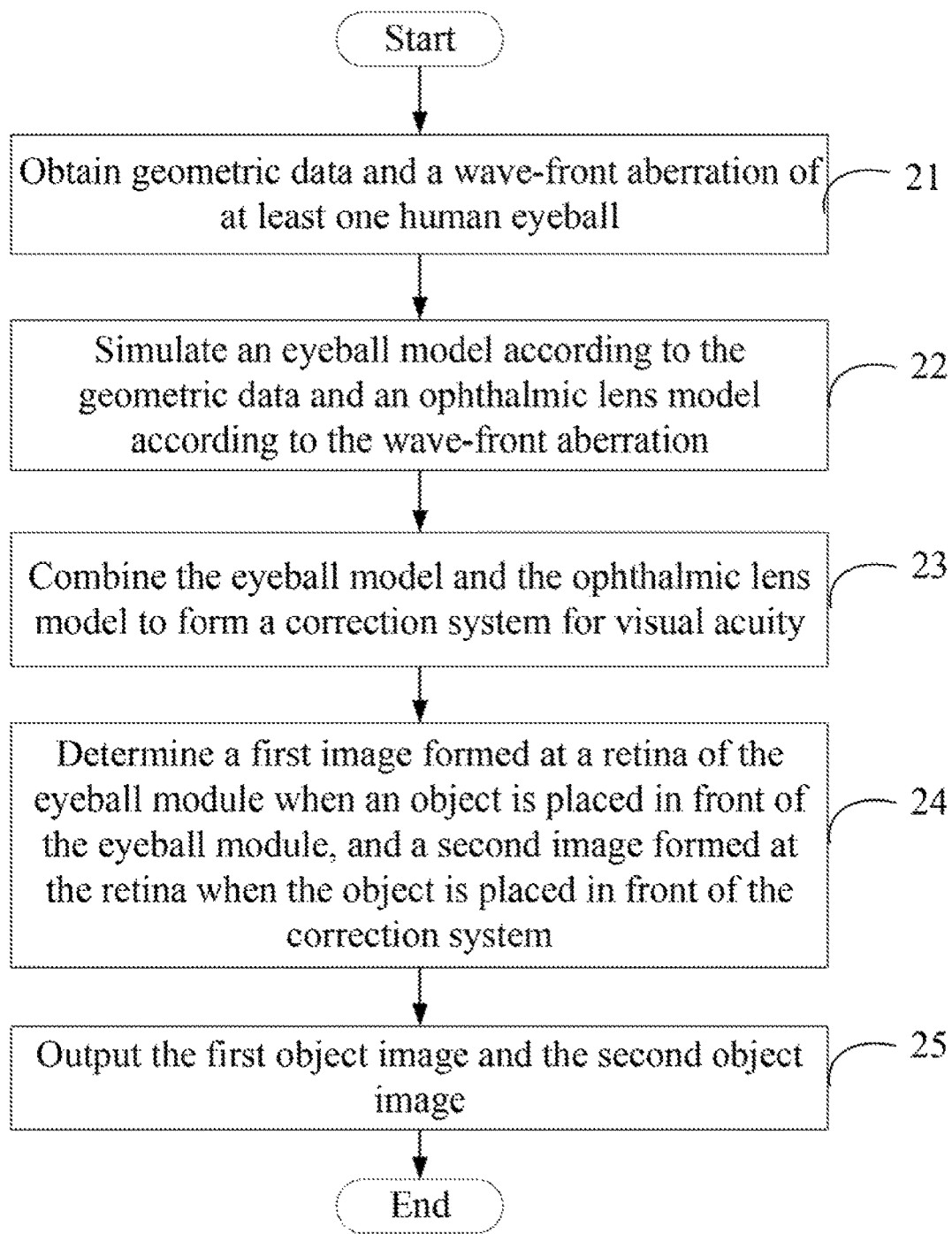
FIG. 2 is a flowchart of an exemplary embodiment of a method for simulating correction of human visual acuity.

FIG. 2 illustrates a flowchart of a method for simulating correction of human visual acuity in accordance with an example embodiment. The method is provided by way of example, as there are a variety of ways to carry out the method. The method described below can be carried out using the configurations illustrated in FIG. 1, for example, and various elements of these figures are referenced in explaining example method. Each block shown in FIG. 2 represents one or more processes, methods or subroutines, carried out in the example method. Furthermore, the illustrated order of blocks is illustrative only and the order of the blocks can change. Additional blocks can be added or fewer blocks may be utilized, without departing from this disclosure. The example method can begin at block 21.

At block 21, a data obtaining module obtains geometric data and a wave-front aberration of at least one human eyeball. In at least one exemplary embodiment, the geometric data comprises central corneal thickness (CCT), anterior chamber depth (ACD), lens thickness (LT), and vitreous chamber depth (VCD), and any combination thereof. The geometric data can further comprise reflective indexes of central corneal, anterior chamber, crystalline lens, and vitreous chamber.

At block 22, a simulation module simulates an eyeball model according to the geometric data and an ophthalmic lens model according to the wave-front aberration. The ophthalmic lens model can be eyeglass model, contact lens model, or intraocular lens model.

At block 23, a combination module combines the eyeball model and the ophthalmic lens model to form a correction system for human visual acuity. In at least one exemplary embodiment, when the ophthalmic lens model is the eyeglass model, the combination module places the eyeglass model in front of the eyeball model to form the correction system. When the ophthalmic lens model is the contact lens model, the combination module places the contact lens model in contact with the eyeball model to form the correction system. When the ophthalmic lens model is the intraocular lens model, the combination module removes the crystalline lens of the eyeball model and embeds the intraocular lens model into the eyeball model to form the correction system.

At block 24, an imaging module determines, according to the convex/concave lens imaging rule, a first image formed at a retina of the eyeball module when an object is placed in front of the eyeball module, and a second image formed at the retina of the eyeball module when the object is placed in front of the correction system.

At block 25, an output module outputs the first object image and the second object image. In at least one exemplary embodiment, the output module outputs the first object image and the second object image to a virtual reality head-mounted display, The embodiments shown and described above are only examples. Many details are often found in the art such as the other features of a protection case. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure up to, and including the full extent established by the broad general meaning of the terms used in the claims. It will therefore be appreciated that the embodiments described above may be modified within the scope of the claims.

What is claimed is:

1. A server for simulating correction of human visual acuity comprising:
at least one processor; and
a memory coupled to the at least one processor and configured to store one or more programs, wherein when executed by the at least one processor, the one or more programs cause the at least one processor to:
obtain geometric data and a wave-front aberration of at least one human eyeball;
simulate an eyeball model according to the geometric data and an ophthalmic lens model according to the wave-front aberration;
combine the eyeball model and the ophthalmic lens model to form a correction system for human visual acuity, wherein the ophthalmic lens model is one of an eyeglass model and a contact lens model, the ophthalmic lens model is placed in front of the eyeball model to form the correction system when the ophthalmic lens model is the eyeglass model, and placed in contact with the eyeball model to form the correction system when the ophthalmic lens model is the contact lens model;
determine, according to a convex/concave lens imaging rule, a first image formed at a retina of the eyeball module when an object being placed in front of the eyeball module, and a second image formed at the retina of the eyeball module when the object being placed in front of the correction system; and
output the first object image and the second object image.

2. The server of claim 1, wherein the geometric data comprises central corneal thickness, anterior chamber depth, lens thickness, and vitreous chamber depth, and any combination thereof.

3. The server of claim 2, wherein the geometric data further comprises reflective indexes of central corneal, anterior chamber, crystalline lens, and vitreous chamber of the at least one human eyeball.

4. The server of claim 1, wherein the server is connected to a first measuring device and a second measuring device; the geometric data and the wave-front aberration are obtained from the first measuring device and the second measuring device, respectively.

5. The server of claim 4, wherein the first measuring device is a handheld tonometer or a non-contact tonometer; the second measuring device is a wave-front aberrometer.

6. The server of claim 1, wherein the server is connected to a virtual reality head-mounted display; the first object image and the second object image are outputted to the virtual reality head-mounted display.

7. A method for simulating correction of human visual acuity comprising:
   obtaining geometric data and a wave-front aberration of at least one human eyeball;
   simulating an eyeball model according to the geometric data and an ophthalmic lens model according to the wave-front aberration;
   combining the eyeball model and the ophthalmic lens model to form a correction system for human visual acuity, wherein the ophthalmic lens model is one of an eyeglass model and a contact lens model, the ophthalmic lens model is placed in front of the eyeball model to form the correction system when the ophthalmic lens model is the eyeglass model, and placed in contact with the eyeball model to form the correction system when the ophthalmic lens model is the contact lens model;
   determining, according to a convex/concave lens imaging rule, a first image formed at a retina of the eyeball module when an object being placed in front of the eyeball module, and a second image formed at the retina of the eyeball module when the object being placed in front of the optical system; and
   outputting the first object image and the second object image.

8. The method of claim 7, wherein the geometric data comprises central corneal thickness, anterior chamber depth, lens thickness, and vitreous chamber depth, and any combination thereof.

9. The method of claim 8, wherein the geometric data further comprises reflective indexes of central corneal, anterior chamber, crystalline lens, and vitreous chamber of the at least one human eyeball.

10. The method of claim 7, wherein the geometric data and the wave-front aberration are obtained from a first measuring device and a second measuring device, respectively.

11. The method of claim 10, wherein the first measuring device is a handheld tonometer or a non-contact tonometer; the second measuring device is a wave-front aberrometer.

12. The method of claim 7, wherein the first object image and the second object image are outputted to a virtual reality head-mounted display.

* * * * *